United States Patent [19]

Bloomer, II et al.

[11] Patent Number: 4,498,329

[45] Date of Patent: Feb. 12, 1985

[54] APPARATUS FOR MEASUREMENT OF SLIDING FRICTION USING GYROSCOPIC MASS

[75] Inventors: James W. Bloomer, II, Bremerton, Wash.; Robert H. Nunn, Plymouth, England

[73] Assignee: The United States of America as represented by the Secretary of the Navy, Washington, D.C.

[21] Appl. No.: 496,699

[22] Filed: May 20, 1983

[51] Int. Cl.³ ............................................ G01N 19/02
[52] U.S. Cl. ......................................................... 73/9
[58] Field of Search .............................................. 73/9

[56] References Cited

U.S. PATENT DOCUMENTS 2,398,156 4/1946 Puterbaugh et al. ..................... 73/9
3,194,051 7/1965 Schnoll ..................................... 73/9
3,511,079 5/1970 Musser ..................................... 73/9

Primary Examiner—S. Clement Swisher
Attorney, Agent, or Firm—R. F. Beers; Charles D. B. Curry; George L. Craig

[57] ABSTRACT

A sphere with a hole through one diameter is held in a spherical chamber within a tube. The axis of the tube and the hole through the sphere are out of alignment by some predetermined angle, $\theta$. The sphere is held within the chamber and the entire unit is caused to spin. The sphere is released while the unit is still spinning. The gyroscopic nutation of the sphere causes the spherical bore to traverse the angle $\theta$ and align with the tubular bore in a time dependent upon the sliding friction between the material of the sphere and the material of the spherical chamber.

10 Claims, 6 Drawing Figures

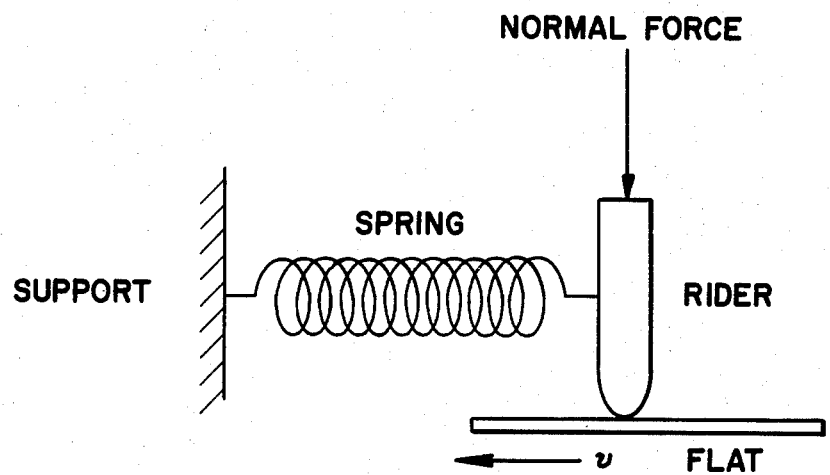
FIG _ 1 (PRIOR ART)
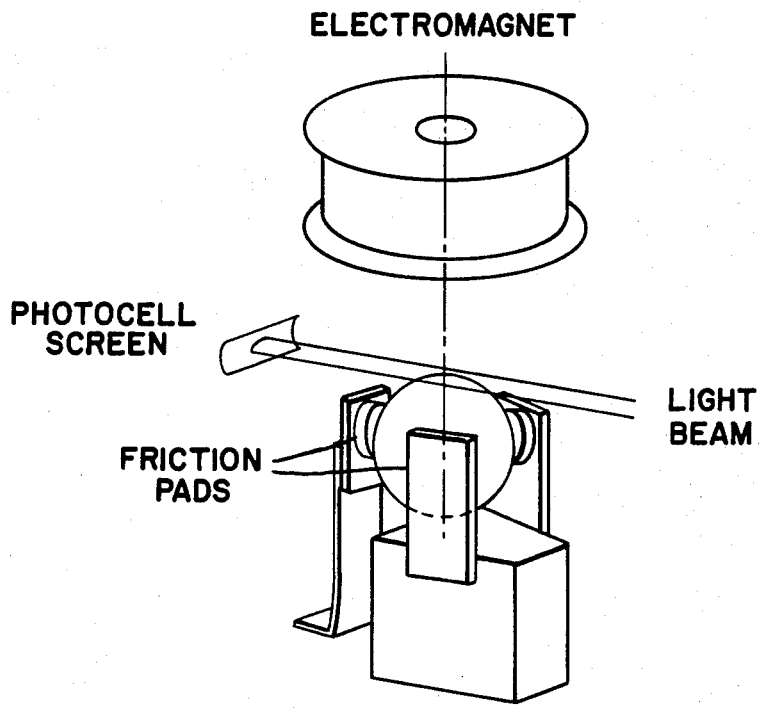
FIG _ 2 (PRIOR ART)

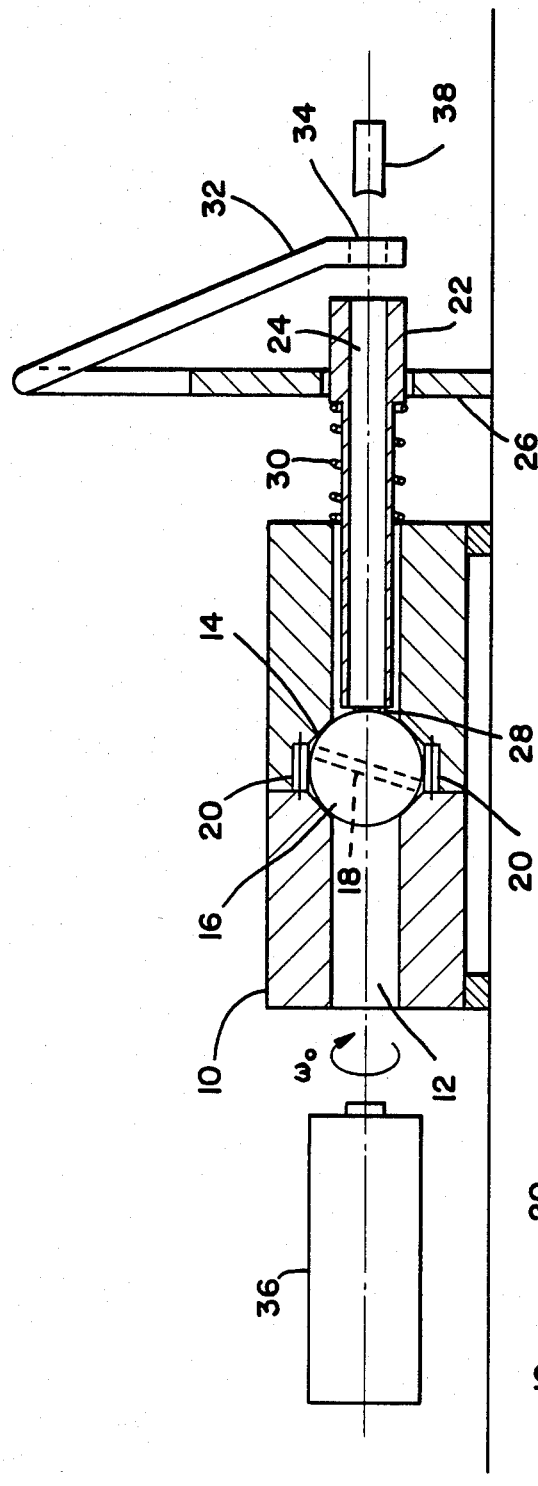
FIG_3
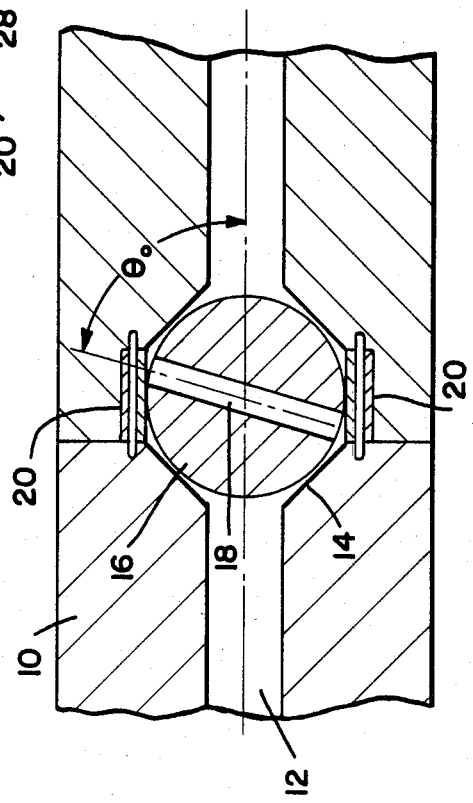
FIG_4

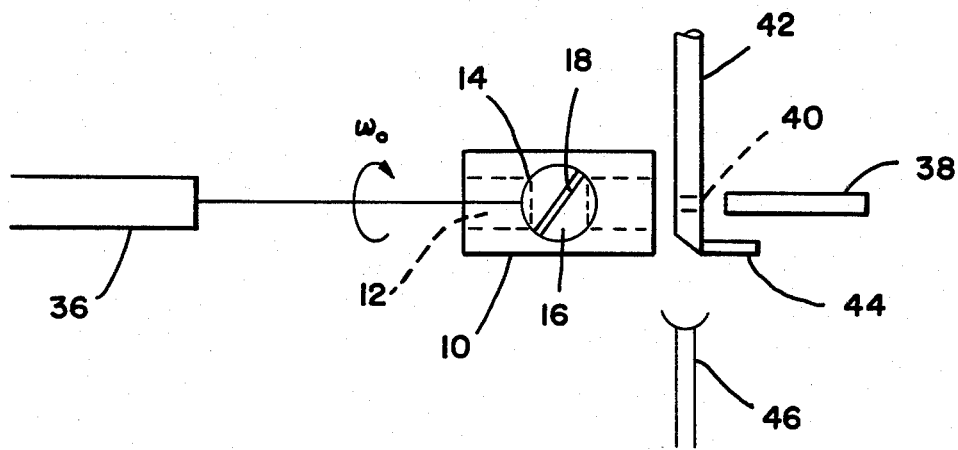
FIG_5A
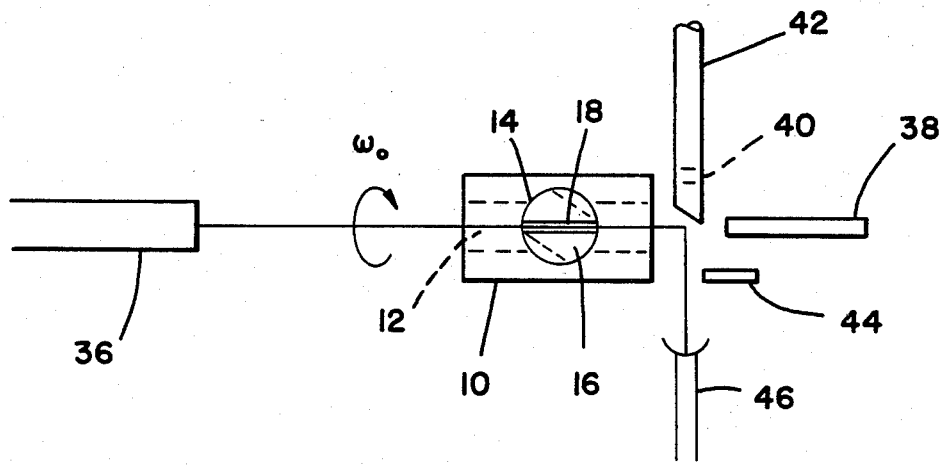
FIG_5B

APPARATUS FOR MEASUREMENT OF SLIDING FRICTION USING GYROSCOPIC MASS

BACKGROUND OF THE INVENTION

1. Field of the Invention

This invention relates to an apparatus and method for measuring sliding friction between two materials. More specifically the invention relates to an apparatus in which a sphere of one material having a bore through one diameter is held within a cavity in a cylinder having a bore; caused to spin within that cavity and the time measured for the spherical bore to align with the cylindrical bore. The time measured is inversely proportional to the coefficient of sliding friction between the material of the sphere and the material of the cavity.

2. Description of Prior Art.

When two bodies in contact are moved relative to one another, the coefficient of sliding friction is given by the ratio of the force required to sustain the motion divided by the normal component of the force holding the two bodies in contact. Measurement of the coefficient of sliding friction is typically accomplished in one of three ways within prior art. For high loads and low sliding speeds, the method shown schematically in FIG. 1 is used. Friction is measured between a flat sliding lower surface and a stationary upper surface called a rider. Movement of the lower surface sets up a frictional force between the two surfaces and the amount of the deflection of the rider is proportional to that force. For high speeds and lighter loads, the rider is pressed against the rim of a revolving disk instead of a flat plate. These devices require careful control of the motion between the rider and the moving surface as well as careful control and measurement of the two pertinent forces. These devices are characteristically complex and subject to inaccuracies due to difficulty in obtaining precise motion control and force or torque measurements while the apparatus is in motion. Other complicating limitations are the existence of static friction, mechanical vibrations and severe frictional heating.

A third method within prior art, shown in FIG. 2, involves suspending a steel ball in the magnetic field of a solenoid with vertical stability maintained by means of a photoelectric feedback system. The freely-suspended ball is then accelerated by a rotating magnetic field of constant frequency in a low-pressure atmosphere between three flat friction pads. Bringing the pads into contact with the steel ball causes rotational deceleration according to the relation:

$$\mu_s = \frac{F}{N} = \frac{I\dot{\omega}}{3RN}$$

where
- $\mu_s$ = coefficient of sliding friction
- F = friction force
- N = Normal force
- I = moment of inertia of the ball
- $\dot{\omega}$ = Angular deceleration of the ball
- R = radius of the ball However this technique, like the others involves complex machinery and difficult, precise motion control and force or torque measurments while in operation. A further limitation is that at least one of the materials for which the measurement is made must be magnetic.

The present invention is of simple construction, requires no complex control of motion, force or torque measurements and requires only the measurement of angular distance traversed and the time elapsed for this increment of motion. Further, the present invention has no problems of mechanical vibration and permits a very great selection of materials, speed of relative motion, surface finishes and operating conditions such as temperature and lubrication of the surfaces.

SUMMARY OF INVENTION

Described is an apparatus and method for measuring the coefficient of sliding friction between a pair of surfaces. A sphere with a hole through one diameter is held in a chamber within a tube. The axis of the tube and the hole through the sphere are out of alignment by a predetermined angle, $\theta$. The sphere is held within the chamber and the entire unit is caused to spin. The sphere is released while the unit is spinning. The gyroscopic nutation of the sphere causes the spherical bore to traverse the angle $\theta$ and align with the tubular bore in a time dependent upon the sliding friction between the material of the sphere and the material of the chamber.

A primary object of invention is to provide a simple compact apparatus and method for measuring the coefficient of sliding friction between two materials.

A further object of invention is to provide an apparatus and method for measuring the coefficient of sliding friction between two materials in which one material is a sphere having a diametrical bore; the other material is a cylinder having a longitudinal bore and a cavity for holding the sphere; and in which the two materials are spun to a predetermined speed after which the sphere is released and allowed to gyroscopically nutate to a position in which the two bores align, the time for which is proportional to the coefficient of sliding friction between the materials.

Yet another object of invention is to provide an apparatus and method for measuring the coefficient of sliding friction between two materials for various conditions of surface finish, temperature or lubrication based upon gyroscopic motion between the two materials.

BRIEF DESCRIPTION OF THE ORIGINAL DRAWINGS

FIG. 1 schematically illustrates one prior art method for determining the coefficient of sliding friction between two bodies.

FIG. 2 schematically illustrates another prior art method for determining the coefficient of sliding friction between two bodies, one of which is magnetic.

FIG. 3 is a schematic of the preferred embodiment of the present invention.

FIG. 4 is a close-up section view of the relationship of the two materials to be tested in the initial position.

FIGS. 5A and 5B are schematics of an alternative embodiment of the present invention.

DESCRIPTION OF THE PREFERRED EMBODIMENT

Referring to FIG. 3, a schematic of the present invention is shown. A two-piece cylindrical assembly 10 having a bore 12 along its longitudinal axis and a central cavity 14 is designed to enclose a sphere 16 having a diametrical bore 18. The sphere 16 loosely fits within the cavity 14 except where it touches two tubular inserts 20. The coefficient of friction to be determined according to the present invention is between the material of the sphere 16 and the material of the tubular inserts 20. A cylindrical plunger 22 configured to slide into the bore 12 at one end of the cylindrical assembly 10 also has a bore 24 along its length coaxially aligned with the bore 12 of the cylindrical assembly 10. The plunger 22 may rotate with the sphere 16 and cylindrical assembly 10 but is otherwise held by a guide 26 such that it may only move along the axis of rotation of the cylindrical assembly 10. Four prongs 28 in one end of the plunger 22 engage four small notches (not shown) in the sphere 16 and are resiliently held in contact by a spring 30 between the cylindrical assembly and a ridge on the plunger 22 by a pendulum weight 32 attached to the guide at one end and having an aperture 34 at the opposite end coaxially aligned with the plunger and cylindrical assembly bores. When the pendulum 32 is moved from the plunger 22, the spring 30 pushes the plunger axially disengaging the prongs 28 from the sphere such that it is free to nutate while a magnetic band (not shown) on the plunger 22 simultaneously actuates a magnetic sensitive diode (not shown) initiating an electric timer (not shown). When the sphere 16 nutates through an angle $\theta$ such that coaxial alignment of the diametrical bore 18 with the cylindrical assembly bore 12 is achieved light from a laser 36 shining down the cylindrical assembly bore 12 is received by a light-sensitive diode 38 positioned opposite the aperture 34 in the pendulum 32 stopping the timer, not shown. An enlarged view of the sphere 16 and the initial orientation within the cavity is shown in FIG. 4.

The sphere 16, by reason of the diametrical bore 18, has a major axis of inertia (coaxial with the bore) and two equal and mutually perpendicular minor axes of inertia. When the sphere 16 and the cylindrical assembly 10 are spun and the major axis of the sphere is not aligned with the axis of rotation, there exists an inertial imbalance of the sphere 16. Thus, when released, the sphere 16 will gyroscopically precess and nutate within the cavity 14 until the diametrical bore (major inertial axis) aligns with the axis of rotation (i.e. coaxial with the cylindrical bore 12. The coefficient of friction, $\mu_s$, between the material of the sphere 16 and the material of the tubular inserts 20 is determined to be proportional to the time elapsed for the diametrical bore 18 to traverse the angular displacement, $\theta$, from alignment with the axis of rotation of the cylindrical assembly 10.

The proportionality between elapsed time and spin rate of the cylindrical assembly 10 for a given angular excursion $(\theta_o - \theta)$ at high values of $\omega_o$ is given by:

$$T = \frac{\omega_o \pi A [(\theta_o - \theta) - \frac{\lambda}{2} \sin 2\theta_o]}{2\mu_s WR \sin \theta_o E(\theta_o)}$$

where
 $\omega_o$ = spin rate of the assembly
 A = sphere mass moment of inertia about the minor axis
 C = sphere mass moment of inertia about the major axis (axis of hole)
 $\theta_o - \theta$ = angle through which the bore of the sphere nutates $\lambda = (C/A) - 1$
 $\mu_s$ = coefficient of friction between the materials tested
 W = weight of the sphere
 R = radius of the sphere
 $E(\theta_o)$ = complete elliptic integral of the second kind with modular angle $\theta_o$.

This may be reduced, for operation of the invention, to the relation:

$$\mu_s = \frac{K\omega_o}{t}$$

$$\text{where } K = \frac{\pi A [(\theta_o - \theta) - \frac{\lambda}{2} \sin 2\theta_o]}{2WR \sin \theta_o E(\theta_o)},$$

a proportionality constant. Therefore, if a sphere 16 of a given material and having known parameters, A, $\lambda$, W, and $\theta$ is spun to a rate $\omega_o$ with the cylindrical assembly 10 and released the coefficient of friction, $\mu_s$, between the material of the sphere 16 and the tubular inserts 20 may be simply determined.

An alternative embodiment of the present invention is shown in FIGS. 5A and 5B. Here, the sphere 16 is initially held within the cavity 14 by an air jet 38 directed through an aperture 40 in a plunger 42 perpendicular to the axis of rotation of the cylindrical assembly 10. A minor segment of the plunger 42 extends beyond the aperture 40 and has a beveled edge contacting a proximity sensor 44. The cylindrical assembly 10 and sphere 16 are spun to the desired speed and a pair of fast-acting solenoids (not shown) simultaneously shut off the air-jet 38; withdraw the plunger 42 until the center of the beveled edge intercepts the imaginary axis of rotation of the cylinder; and start an electrical timer when the plunger 42 breaks contact with the proximity sensor 44. After an elapsed time, $\tau$, the diametrical bore 18 aligns with the cylindrical bore 12 permitting light from the laser 36 to transit the bore 12 an reflect off the beveled edge into a light-sensitive diode 46. This simultaneously stops the timer.

The present invention has been practiced using air driven turbines and electric motors with flexible couplings to drive the cylindrical assembly. The sphere has been given a preferential moment of inertia by means of a diametrical bore although other methods of mass distribution may be used to achieve the same effect. The cavity containing the sphere has been spherical and formed of one of the materials of interest as shown in FIG. 5 or octagonal with tubular inserts for ease in testing a variety of materials as in FIGS. 3 and 4. Clearly the invention as taught by the specification and drawings suggest a variety of arrangements which may be practiced by those skilled in the art without departing from the spirit and scope of the invention.

What is claimed is:

1. An apparatus for measuring the coefficient of sliding friction between two materials comprising:
 (a) a cylinder having a bore along the longitudinal axis and capable of being rotated at selected speeds about said longitudinal axis, said cylinder configured as two pieces separably fastened at the center of said cylinder, said cylinder having a central cavity of larger dimension than said bore located approximate the center of said cylinder;
 (b) a sphere configured to fit with close tolerance inside said cavity, said sphere designed to have two equal minor axes of inertia and a major axis of inertia selectably alignable a predetermined amount from said longitudinal axis of said cylinder;
 (c) means for releasably holding said sphere within said cavity inside said cylinder until said sphere and said cylinder are rotating at a predetermined rate;

(d) means for determining when said sphere is released from selected alignment within said cavity.

(e) means for detecting when said major axis of inertia of said sphere inside said cavity is coaxial with said longitudinal axis of said cylinder.

2. The apparatus of claim 1 wherein said holding means comprises:

(a) a cylindrical plunger configured to slidably fit within said bore of said cylinder, said plunger having a bore along its longitudinal axis coaxial with said bore of said cylinder;

(b) at least two prongs at one end of said plunger for releaseable engagement with said sphere;

(c) means for holding said plunger such that only motion along or about said longitudinal axis is permitted;

(d) a spring positioned between said cylinder and a ridge about said plunger adjacent said holding means and about said plunger, said spring resiliently pushing said plunger away from said sphere; and (e) means for releasably pressing said plunger against said spring to hold said prongs on said plunger in contact with said sphere.

3. The apparatus of claim 1 wherein said holding means comprises:

(a) an air jet directing a stream of air into said bore of said cylinder to hold said sphere in a predetermined orientation within said cavity while said cylinder and said sphere are rotated; and (b) mean for selectively stopping said air jet such that said sphere is released within said cavity.

4. The apparatus of claim 1 wherein said detecting means comprises:

(a) a laser directing a beam down said bore of said cylinder in the direction of said holding means; and (b) means for receiving said laser radiation when said major inertial axis of said sphere is aligned with said cylindrical bore such that said radiation transits the length of said bore.

5. The apparatus of claim 1 in which said cavity of said cylinder is spherical and the cavity walls are made of one of said materials to be tested.

6. The apparatus of claim 1 in which said cavity of said cylinder is configured to hold at least two tubular inserts of one of said materials to be tested, said tubular inserts having the only surfaces in said contact with said sphere.

7. A method for determining the coefficient of sliding friction between two bodies comprising the steps of:

(a) configuring the first of said bodies as a cylinder, said cylinder having an internal bore along its longitudinal axis and capable of being rotated at selected speeds about said axis, said cylinder further fabricated in two pieces such that said cylinder has a central cavity approximate the middle of said axis;

(b) configuring the second of said bodies as a sphere having a major axis of inertia and two equal minor axis of inertia, the diameter of said sphere being slightly less than any dimension of said cavity;

(c) placing at least two tubular inserts in fixed positions in said cavity such that said inserts touch the surface of said sphere;

(d) aligning said major axis of said sphere at a predetermined angle away from said axis of said cylinder;

(e) holding said sphere at said predetermined angle while said cylinder and said sphere within said cavity are spun to a predetermined rate of rotation;

(f) releasing said sphere in said cavity such that said sphere will gyroscopically align said major axis of inertia with said axis of said cylinder; and (g) determining the time required for said major axis of inertia of said sphere to traverse said predetermined angle and align with said cylindrical axis.

8. The method of claim 7 wherein said major axis of inertia of said sphere is defined by a diametrical bore through said sphere.

9. The method of claim 7 wherein said sphere is releasably held within said cavity of said cylinder by a cylindrical plunger free to rotate with said sphere and slidably moveable along said axis and within said bore of said cylinder, said plunger resiliently holding said sphere in place until said predetermined rotation rate is achieved.

10. The method of claim 7 wherein said sphere is releasably held within said cavity of said cylinder by a selectively actuated air jet.

* * * * *